United States Patent [19]

Michaely

[11] Patent Number: 4,957,538
[45] Date of Patent: Sep. 18, 1990

[54] CERTAIN 2-(2',3',4'-TRISUBSTITUTED BENZOYL)-1,3-CYCLOOHEXANEDIONES

[75] Inventor: William J. Michaely, El Cerrito, Calif.

[73] Assignee: ICI Americas Inc., Wilmington, Del.

[21] Appl. No.: 273,371

[22] Filed: Nov. 18, 1988

[51] Int. Cl.⁵ .................. A01N 31/14; C07C 323/65
[52] U.S. Cl. ........................... 71/98; 71/103; 71/122; 71/123; 568/29; 568/30; 568/31; 568/43; 568/306; 568/329
[58] Field of Search .................. 568/29, 30, 31, 43, 568/306, 329; 71/98, 103, 122, 123

[56] References Cited

U.S. PATENT DOCUMENTS 4,797,150  1/1989  Carter ........................... 71/103

FOREIGN PATENT DOCUMENTS

| 5709 | 12/1979 | European Pat. Off. | 71/103 |
| 135191 | 3/1985 | European Pat. Off. | 568/31 |
| 137963 | 4/1985 | European Pat. Off. | |
| 264859 | 4/1988 | European Pat. Off. | 568/30 |
| 268795 | 6/1988 | European Pat. Off. | 568/31 |

Primary Examiner—Mary E. Ceperley
Attorney, Agent, or Firm—Edwin H. Baker

[57] ABSTRACT

Herbicidal compounds of the structural formula

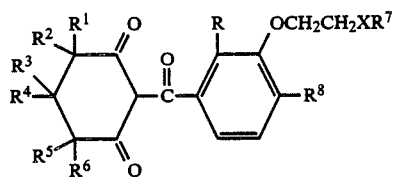

wherein X is oxygen or sulfur; R is chlorine or bromine; $R^1$ is hydrogen or $C_1$-$C_4$ alkyl; $R^2$ is hydrogen or $C_1$-$C_4$ alkyl; $R^3$ is hydrogen or $C_1$-$C_4$ alkyl; $R^4$ is hydroxy, hydrogen or $C_1$-$C_4$ alkyl; or $R^3$ and $R^4$ together are carbonyl (=O) with the proviso that $R^1$, $R^2$, $R^5$ and $R^6$ are all $C_1$-$C_4$ alkyl; $R^5$ is hydrogen or $C_1$-$C_4$ alkyl; $R^6$ is hydrogen, $C_1$-$C_4$ alkyl, $C_1$-$C_4$ alkylthio, or $C_1$-$C_4$ alkylsulfonyl, with the proviso that when $R^6$ is $C_1$-$C_4$ alkylthio or $C_1$-$C_4$ alkylsulfonyl, then $R^3$ and $R^4$ are not together carbonyl; $R^7$ is methyl or ethyl; and $R^8$ is (1) halogen; (2) nitro; or (3) $R^bSO_n$—wherein n is the integer 0 or 2; and $R^b$ is (a) $C_1$-$C_3$ alkyl; and their salts.

24 Claims, No Drawings

CERTAIN 2-(2',3',4'-TRISUBSTITUTED BENZOYL)-1,3-CYCLOOHEXANEDIONES

BACKGROUND OF THE INVENTION

European Patent Publication Nos. 0,135,191 and 0,137,963 were published Mar. 27, 1985 and Apr. 24, 1985, respectively, and relate to certain prior art 2-(2-halogen substituted benzoyl)-1-3-cyclohexane-1,3-diones as herbicides. The compounds can have the following structural formula

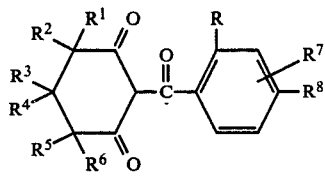

wherein R through $R^8$ are substantially the same as defined below and $R^7$ can be alkoxy.

The compounds of the present invention have unexpectedly superior herbicidal activity over the cited prior art compounds or give unexpectedly reduced injury to crop plants.

DESCRIPTION OF THE INVENTION

This invention relates to 2-(2',3', 4'-trisubstituted benzoyl)-1,3-cyclohexanediones, their use as herbicides and herbicidal compositions containing the compounds.

Embodied within the scope of this invention are novel compounds having the following structural formula wherein
X is oxygen or sulfur, preferably oxygen;
R is chlorine or bromine;
$R^1$ is hydrogen or $C_1$–$C_4$ alkyl, preferably methyl;
$R^2$ is hydrogen or $C_1$–$C_4$ alkyl, preferably methyl;
$R^3$ is hydrogen or $C_1$–$C_4$ alkyl, preferably methyl;
$R^4$ is hydroxy, hydrogen or $C_1$–$C_4$ alkyl, preferably methyl; or $R^3$ and $R^4$ together are carbonyl (=O) with the proviso that $R^1$, $R^2$, $R^5$ and $R^6$ are $C_1$–$C_4$ alkyl, preferably all methyl;
$R^5$ is hydrogen or $C_1$–$C_4$ alkyl, preferably methyl;
$R^6$ is hydrogen, $C_1$–$C_4$ alkyl, preferably methyl, $C_1$–$C_4$ alkylthio, preferably methylthio or $C_1$–$C_4$ alkylsulfonyl, preferably methylsulfonyl, with the proviso that when $R^6$ is $C_1$–$C_4$ alkylthio or $C_1$–$C_4$ alkylsulfonyl, then $R^3$ and $R^4$ are not together carbonyl;
$R^7$ is methyl or ethyl; and
$R^8$ is (1) halogen, preferably chlorine or bromine; (2) nitro; or (3) $R^bSO_n$— wherein n is the integer 0 or 2, preferably 2, and $R^b$ is (a) $C_1$–$C_3$ alkyl, preferably methyl or ethyl.

The term "$C_1$–$C_4$ alkyl" includes methyl, ethyl, n-propyl, isopropyl, n-butyl, sec-butyl, isobutyl and t-butyl. The term "halogen" includes chlorine, bromine, iodine and fluorine. The term "$C_1$–$C_4$ alkoxy" includes methoxy, ethoxy, n-propoxy, isopropoxy, n-butoxy, sec-butoxy, isobutoxy and t-butoxy. The term "haloalkyl" includes the eight alkyl groups with one or more hydrogens replaced by chloro, bromo, iodo or fluoro.

Salts of the above-described compounds (as defined hereinafter) are also the subject of the instant invention.

The compounds of this invention can have the following four structural formula because of tautomerism:

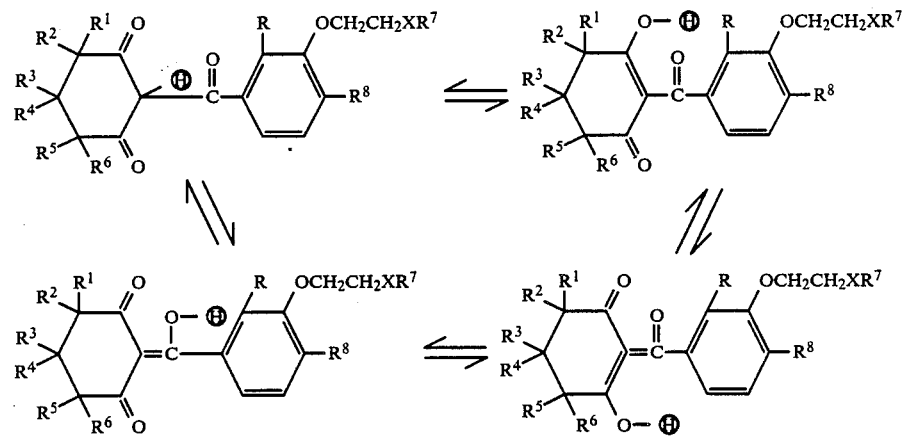

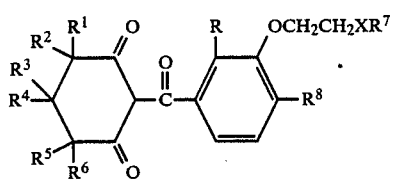

wherein X, R, $R^1$, $R^2$, $R^3$, $R^4$, $R^5$, $R^6$, $R^7$ and $R^8$ are as defined above.

The circled proton on each of the four tautomers is reasonably labile. These protons are acidic and can be removed by any base to give a salt having an anion of the following four resonance forms:

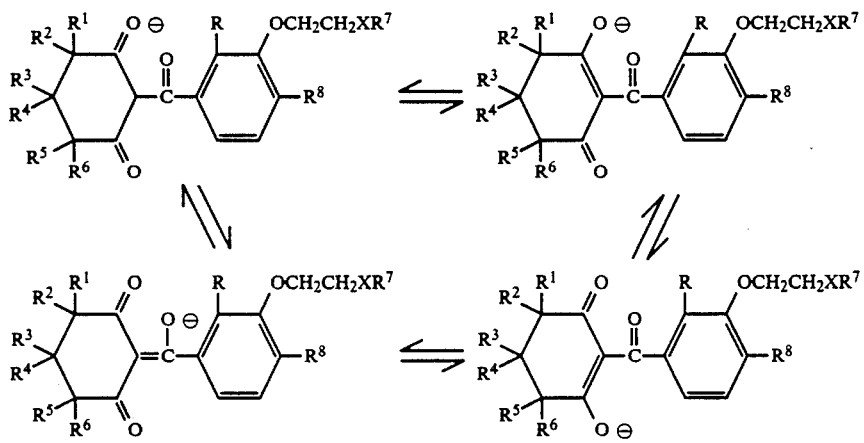

wherein X, R, R¹, R², R³, R⁴, R⁵, R⁶, R⁷ and R⁸ are as defined above.

Examples of cations of these bases are inorganic cations such as alkali metals e.g. lithium, sodium, sodium, and potassium or organic cations such as substituted ammonium, sulfonium or phosphonium wherein the substituent is an aliphatic or aromatic group.

The compounds of this invention and their salts are active herbicides of a general type. That is, they are herbicidally effective against a wide range of plant species. The method of controlling undesirable vegetation of the present invention comprises applying an herbicidally effective amount of the above-described compounds to the area control is desired.

The compounds of the present invention can be prepared by the following two-step general method.

The process proceeds via the production of an enol ester intermediate as shown in reaction (1). The final product is obtained by rearrangement of the enol ester as shown in reaction (2). The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

wherein X and R through R⁸ are as defined and Y is halogen, preferably chlorine, $C_1-C_4$ alkyl—C(O)—O—, $C_1-C_4$ alkoxy—C(O)— or

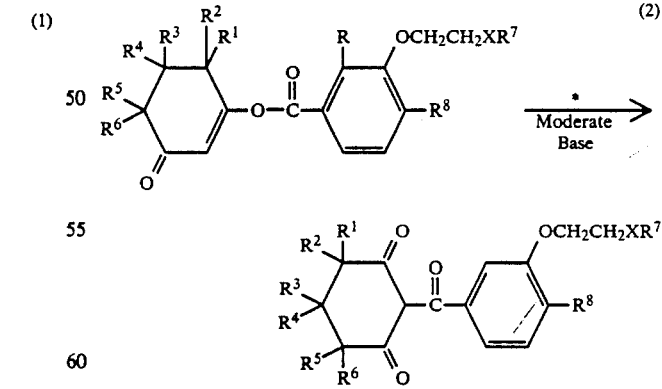

wherein X, R, R⁷ and R⁸ in this portion of the molecule are identical with those in the reactant shown above and the moderate base is as defined, preferably tri-$C_1-C_6$ alkylamine, pyridine, alkali metal carbonate or alkali metal phosphate.

Generally, in step (1) mole amounts of the dione and substituted benzoyl reactant are used, along with a mole amount or excess of the base. The two reactants are combined in an organic solvent such as methylene chloride, toluene, ethyl acetate or dimethylformamide. The base or benzoyl reactant preferably are added to the reaction mixture with cooling. The mixture is stirred at 0° C.–50° C. until the reaction is substantially complete.

The reaction product is worked up by conventional techniques.

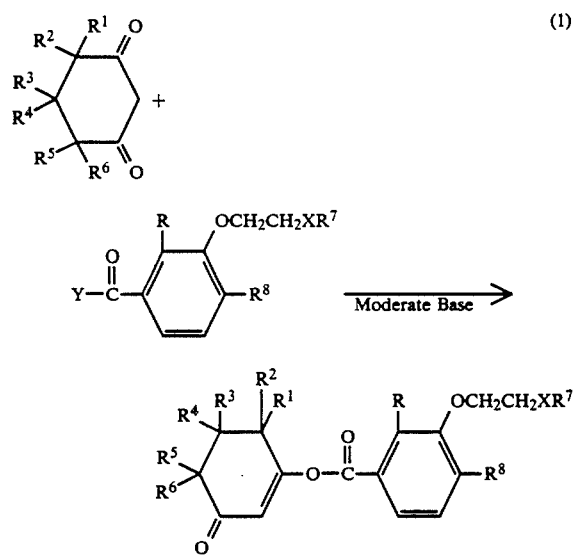

\* = Cyanide source.
Moderate base = as defined herein.

wherein X and R through R⁸ are as defined.

Generally, in step (2) a mole of the enol ester intermediate is reacted with 1 to 4 moles of the base, preferably about 2 moles of moderate base and from 0.01 mole to about 0.5 mole or higher, preferably around 0.1 mole of the cyanide source (e.g., potassium cyanide or acetone cyanohydrin). The mixture is stirred in a reaction pot until the rearrangement is substantially complete at a temperature below 80° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

The process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1-4 carbon atoms in the alkyl groups, such as acetone or methyl isobutyl ketone cyanohydrins; cyanohydrins of benzaldehyde or of $C_2$-$C_5$ aliphatic aldehydes such as acetaldehyde, propionaldehyde, etc., cyanohydrins; zinc cyanide; tri(lower alkyl) silyl cyanides, notably trimethyl silyl cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher catalyst levels of about 2 mole percent. Generally about 1–10 mole % of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this embodiment include both organic bases such as tertiary amines and inorganic bases such as alkali metal carbonates and phosphates. Suitable tertiary amines include trialkylamines such as triethylamine, trialkanolamines such as triethanolamine, and pyridine. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the Crown ethers.

A number of different solvents may be usable in this process, depending on the nature of the acid chloride or the acylated product. A preferred solvent for this reaction is 1,2-dichloroethane. Other solvents which may be employed, depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures up to about 50° C.

The above described substituted benzoyl chlorides can be prepared from the corresponding substituted benzoic acids according to the teaching of Reagents for Organic Synthesis, Vol. I, L. F. Fieser and M. Fieser, pp. 767–769 (1967).

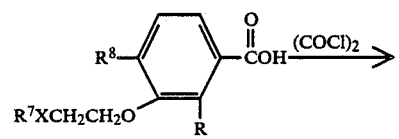

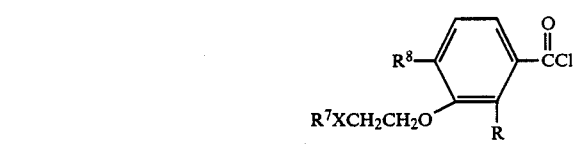

wherein X, R, $R^7$ and $R^8$ are as previously defined.

The above-described 5-hydroxy-4,4,6,6-tetra-substituted 1,3-cyclohexanediones can be prepared according to reaction (d).

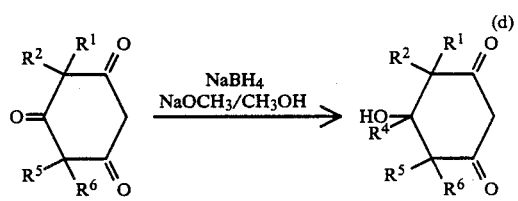

wherein $R^1$, $R^1$, $R^5$ and $R^6$ are as defined and $R^4$ is hydrogen.

In reaction (d) $NaBH_4$ is added to a basic methanolic solution of the syncarpic acid under controlled conditions and reacted at room temperature. The reaction solution is acidified and the product recovered by conventional techniques.

When $R^7$ is $C_1$-$C_4$ alkyl, $C_2$-$C_5$ alkenyl, $C_2$-$C_5$ alkynyl or cyano, the dione can be prepared by reacting a nucleophile such as methyl lithium with a 4,4,6,6-tetra-substituted 1,3,5-cyclohexanetrione as displayed in reaction (e).

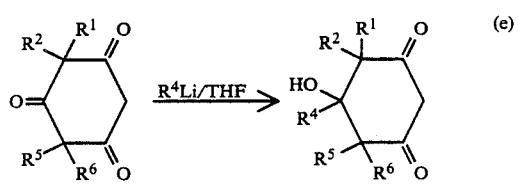

wherein $R^1$, $R^2$, $R^4$, $R^5$ and $R^6$ are as defined and $R^4$ is $C_1$-$C_4$ alkyl, $C_2$-$C_5$ alkenyl, $C_2$-$C_5$ alkynyl or cyano.

In reaction (e) the lithium compound is added to a solution of the syncarpic acid reactant under controlled conditions and reacted at room temperature. The reaction solution is then acidified and the product recovered by conventional techniques.

The substituted 1,3-cyclohexanediones of the formula

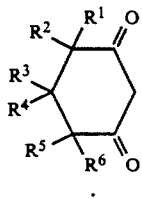

where $R^1$ through $R^5$ are as defined and $R^6$ is $C_1-C_4$ alkylthio or $C_1-C_4$ alkylsulfonyl can be prepared by a wide variety of general methods according to the teachings of *Modern Synthetic Reactions*, 2nd Edition, Chapter 9, H. O. House, W. A. Benjamin, Inc., Menlo Park, Calif. (1972).

The trisubstituted benzoic acid chloride intermediates are prepared by the general method shown in FIG. I of the next page wherein $R^{10}$ is $C_1-C_2$ alkyl, preferably methyl; formyl; cyano; carboxy or —$CO_2R^a$ where $R^a$ is $C_1-C_4$ alkyl, preferably ethyl; most preferably $R^{10}$ is —$CO_2C_2H_5$; $R^{11}$ is —$CH_2CH_2OCH_3$; —$CH_2CH_2OC_2H_5$; —$CH_2CH_2SCH_3$ or —$CH_2CH_2SC_2H_5$; $R^{12}$ is $C_1-C_4$ alkyl, preferably methyl, ethyl or n-propyl; and $R^{15}$ is —$CH_2CH_2OCH_3$ or —$CH_2CH_2OC_2H_5$. $R^x$ and $R^z$ are $C_1-C_4$ alkyl. The X of $R^{11}X$ stands for halogen, preferably chlorine or iodine.

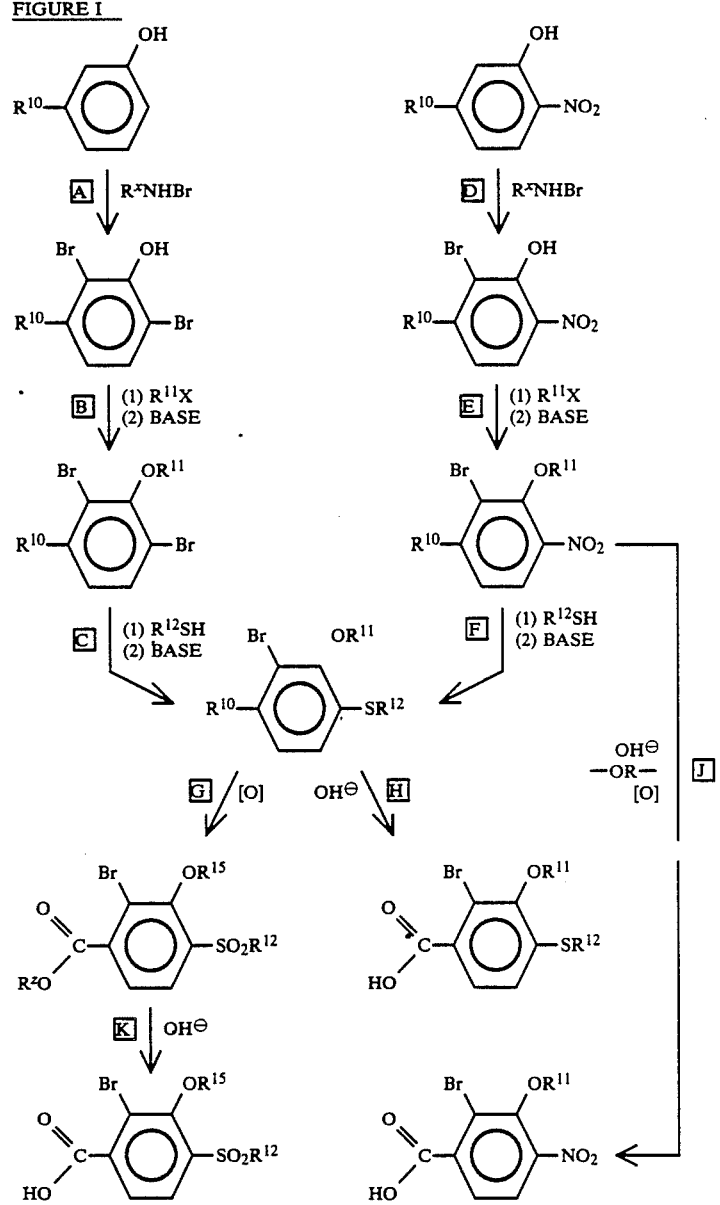

FIGURE I

Referring to FIG. I, and particularly to Reaction Steps (A) through (K), consider the following:

Generally in Reaction Step (A), a mole amount of the 3-substituted phenol is reacted with 2 moles of the brominating agent N-bromo $C_1-C_4$ alkylamine, preferably N-bromo tetra-butyl amine in a solvent such as methylene chloride at a temperature between —70° C. to 25° C. After this reaction, the free brominated phenol is formed by reaction with a strong acid such as HCl. The N-bromo $C_1-C_4$ alkyl amine can be prepared by a reaction of 2 moles of $C_1-C_4$ alkyl amine and a mole of bromine in a solvent such as methylene chloride at low temperatures to yield one mole of N-bromo $C_1-C_4$ alkyl amine. The final reaction product is recovered by conventional techniques.

For Reaction Step (B), one mole of the dibromo-substituted phenol reaction product of Step (A) is reacted with an appropriate alkylating agent such as a 2-chloroethyl ethyl ether, 2-chloroethyl methyl ether, 2-chloroethyl methyl sulfide, 2-chloroethyl ethyl sulfide or $C_1$–$C_4$ alkylchloride along with a catalytic amount of potassium iodide and a mole excess of a base such as potassium carbonate. Alkyl iodides such as methyl iodide or ethyl iodide may also be used. In these cases the catalytic potassium iodide is not needed and little or no heat is required. The reaction is run at 50° C. to 80° C. for 4 hours with agitation. The reaction product is recovered by conventional techniques.

For Reaction Step (C), the dibromo compound from Reaction Step (B) is reacted with an equal mole amount of a $C_1$–$C_4$ alkyl mercaptan along with a mole excess of a base such as potassium carbonate in a solvent such as dimethylformamide. The reaction is run for several hours at a temperature between 50° C. to 100° C. with stirring under an inert atmosphere such as nitrogen. The desired reaction product is recovered by conventional techniques.

Generally, in Reaction Step (D), a mole amount of the 2-nitro-4-substituted phenol is monobrominated with a mole amount of the brominating agent N-bromo-$C_1$–$C_4$-alkyl amine according to the general procedure described for Reaction Step (A). 3-hydroxy-4-nitrobenzoic acid is the least preferred reactant because it results in a less pure preparation of 2-bromo-3- hydroxy-4-nitrobenzoic acid. Preferably an alkyl ester of 3-hydroxy-4-nitrobenzoic acid is used. The ester can be prepared by conventional synthesis using concentrated sulfuric acid in a solution of alkanol such as ethanol.

Reaction Step (E) is run using the general procedure of Step (B). Mole amounts of the phenol and the alkylating agent are used.

For Reaction Step (F) the procedure of Step (C) is used. The displacement of the nitro group by the mercaptan is essentially quantitative and occurs at temperatures from 0° C. to 25° C.

For Reaction Step (G) a mole amount of the alkyl ester of 2-bromo-4-alkylthio benzoic compound is oxidized with at least 3 moles of an oxidizing agent such as m-chloroperbenzoic acid in a suitable solvent such as methylene chloride by stirring a solution of the reactants at 20° to 100° C. The desired intermediate is recovered by conventional techniques. During this reaction step the alkylthio substituent is oxidized to the corresponding alkylsulfone.

For Reaction Step (H) a mole amount of the 2-bromo-3-substituted-4-alkylthio ester or cyano compound is hydrolyzed with a base such as sodium hydroxide to the corresponding 2-bromo-3-substituted-4-alkylthio benzoic acid. The hydrolysis is run in a solvent such as an 80 percent methanol-water mixture. The reaction can be run at 25°–100° C. with stirring. The desired product is recovered by conventional techniques.

For Reaction Step (J) when "$R^{10}$" is cyano or an ester group a mole amount of the appropriate 2-bromo-3-substituted-4-nitro compound is hydrolyzed with a base such as sodium hydroxide to the corresponding 2-bromo-3-substituted-4-nitro benzoic acid. The hydrolysis is run in a solvent such as an 80 percent methanol-water mixture. The reaction can be run at 25°–100° C. with stirring. The desired product is recovered by conventional techniques. When "$R^{10}$" is formyl, methyl or ethyl, a mole amount of the appropriate 2-bromo-3-substituted-4-nitro compound is oxidized to the corresponding trisubstituted benzoic acid with an excess of an oxidizing agent such as potassium permanganate or sodium hypochloride according to the known procedures.

For Reaction Step (K) the alkyl ester of the trisubstituted benzoic acid is converted to the trisubstituted benzoic acid by the hydrolysis step taught in Reaction Step (H).

The intermediate benzoic acids described herein can easily be converted to their respective acid chlorides and then to their acid cyanides, if desired, by the following two reactions. First, a mole of oxalyl chloride and a catalytic amount of dimethylformamide in a suitable solvent such as methylene chloride at a temperature of 20° to 40° C. for 1 to 4 hours is heated with a mole of the intermediate benzoic acid. The corresponding benzoic acid cyanide can easily be prepared from the benzoic acid chloride by reaction with cuprous cyanide at a temperature of 50° to 220° C. for 1 to 2 hours.

The trisubstituted benzoic acid chloride intermediates are useful in the preparation of the previously described herbicidal 2-(2', 3', 4'- trisubstituted benzoyl)-1,3-cyclohexanediones.

The following series of examples teach the synthesis of representative intermediate compounds of this invention. The structures of all compounds of the examples and tables were verified by nuclear magnetic resonance (NMR), infrared spectroscopy (IR) and mass spectroscopy (MS).

EXAMPLE 1

Ethyl 2,4-dibromo-3-hydroxybenzoate

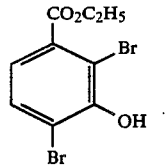

Using a procedure similar to that described (D. E. Pearson, R. D. Wysong and C. V. Breder in *J. Org. Chem.* 32, 2358 [1967]), to a 1-liter, 3-neck flask equipped with a mechanical stirrer, a nitrogen inlet and a pressure equalizing addition funnel was added 59 grams (g) of t-butyl amine (0.8 mole) in 400 milliliters (mL) of methylene chloride. This mixture was cooled to −65° C. with dry ice/isopropanol. To the cooled solution was slowly added (1 hour) 64 grams (0.4 mole [m]) of bromine diluted in 50 mL of methylene chloride. After the addition was complete, the mixture was stirred for 1 hour at approximately −60° C. Ethyl 3-hydroxyenzoate (0.2 mole 33.2 grams) was added, in one portion, to the cooled reaction mixture. This mixture was allowed to warm to room temperature overnight. The white solid was filtered off and washed with a minimum amount of methylene chloride and converted to the free phenol (ethyl 2,4-dibromo-3-hydroxybenzoate) using 500 mL methylene chloride and 400 mL of 2 Normal (N) hydrochloric acid. Gas chromatography indicated the product (49 g) was 92% pure. This material was a viscous oil.

Additional compounds were prepared by the same procedure as described in Example 1 and are listed in Table 1.

TABLE 1

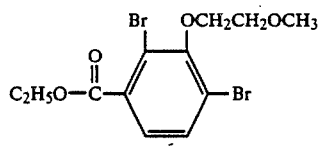

| R[10] | Physical Constant (m.p. °C.) |
|---|---|
| CN | 194–198 |
| CO$_2$CH$_3$ | 74–75 |
| CO$_2$H | 198–200 |
| CHO | 135–136 |
| CF$_3$ | 58–61 |

EXAMPLE 2

Ethyl 2,4-dibromo-3-(2-methoxyethoxy) benzoate

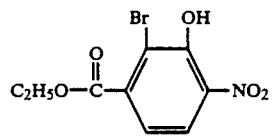

The ethyl ester from Example 1 (32.4 g, 0.1 mole) was dissolved in 200 mL of dimethyl formamide (DMF) and an excess of potassium carbonate (27.6 g, 0.2 mole) and 2-chloroethyl methyl ether (18.8 g, 0.2 mole) along with a catalytic amount of potassium iodide (4.8 g, 0.03 mole) were added. This reaction mixture was vigorously stirred and maintained at 70° C. for 4 hours. Normal workup gave 31.8 g of ethyl 2,4-dibromo-3-(2-methoxyethoxy) benzoate as an oil, 94% pure by gas chromatography. This ester would readily be hydrolyzed to its acid via the method described in Example 7.

Additional compounds were prepared by the same procedure as described in Example 2 (except in those cases using an alkyl iodide, the potassium iodide catalyst was omitted and little or no heat was required) and are listed in Table 2.

TABLE 2

| R[10] | R[11] | Physical Constant (m.p. °C.) |
|---|---|---|
| CO$_2$H | C$_2$H$_4$OC$_2$H$_5$ | 65–70 |
| CO$_2$H | C$_2$H$_4$SCH$_3$ | oil |
| CO$_2$H | C$_2$H$_4$OCH$_3$ | 75–80 |
| CO$_2$C$_2$H$_5$ | C$_2$H$_4$SCH$_3$ | oil |

EXAMPLE 3

Ethyl 2-bromo-3-(2-methoxyethoxy)-4-ethylthiobenzoate

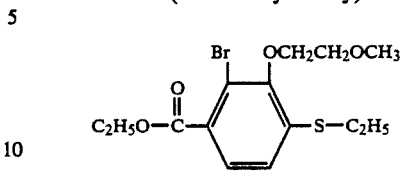

Ethyl 2,4-dibromo-3-(2-methoxyethoxy) benzoate (15.3 g, 0.04 mole) was dissolved in 125 mL of DMF and potassium carbonate (13.8 g, 0.1 mole) and ethyl mercaptan (4 g, 0.064 mole) were added. This mixture was heated at 70° C., under nitrogen, with vigorous stirring, for 4 hours. Normal workup gave 14.3 g of crude product (82% desired product by gas chromatography), ethyl 1 bromo-3-(2-methoxyethoxy)-4-ethylthiobenzoate as a viscous oil. This ester could readily, be hydrolyzed to its free acid via the method described in Example 7. The crude ester was purified via silica chromatography using ether/pentane to give 11.2 g of pure product as an oil. The above-prepared ester was hydrolyzed to the corresponding acid according to the procedure described in Example 8.

Additional compounds were prepared by the same procedures as described in Example 3 and are listed in Table 3.

TABLE 3

| R[10] | R[11] | R[12] | Physical Constant (m.p. °C.) |
|---|---|---|---|
| CO$_2$C$_2$H$_5$ | C$_2$H$_4$SCH$_3$ | C$_2$H$_5$ | oil |
| CO$_2$C$_2$H$_5$ | C$_2$H$_4$OCH$_3$ | CH$_3$ | oil |
| CO$_2$C$_2$H$_5$ | C$_2$H$_4$OC$_2$H$_5$ | CH$_3$ | oil |
| CO$_2$C$_2$H$_5$ | C$_2$H$_4$OCH$_3$ | n-C$_3$H$_7$ | oil |

EXAMPLE 4

Ethyl 2-bromo-3-hydroxy-4-nitrobenzoate

A 0.1 mole of the ethyl ester of 3-hydroxy-4-nitrobenzoic acid was monobrominated using the procedure described in Example 1, except only one equivalent of bromine and two equivalents of t-butyl amine were used. This reaction yielded ethyl 2-bromo-3-hydroxy-4-nitrobenzoate in 70.1% yield. It had a melting point of 58°–61° C.

The ethyl ester of 3-hydroxy-4-nitrobenzoic acid was prepared as follows:

To 100 g of 3-hydroxy-4-nitrobenzoic acid in 300 mL of ethanol was added 15 mL of concentrated sulfuric acid. This solution was refluxed for 3 hours and then a Dean-Stark trap was attached and 100 mL of ethanol-water was distilled off. The reaction mixture was cooled and poured onto 500 grams of ice. The resulting solid was collected, dissolved in 500 mL of ether and the ether solution was washed three times with 1% aqueous sodium bicarbonate. The ether layer was dried and concentrated to give 103.8 g of pure ester.

EXAMPLE 5

Ethyl 2-bromo-3-(2-methoxyethoxy)-4-nitrobenzoate

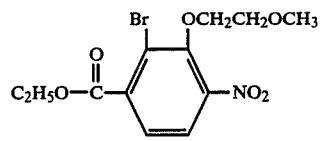

Using a procedure similar to that of Example 2, 0.2 moles of ethyl 2-bromo-3-hydroxy-4-nitrobenzoate and an excess of potassium carbonate (0.35 moles) and 2-chloroethyl methyl ether (0.35 moles) along with a catalytic amount of potassium iodide (7.2 g, 0.045 m) were combined with 350 mL of dimethylformamide. After heating at 70° C. for 4 hours, normal workup gave 0.187 moles of ethyl 2-bromo-3-(2-methoxyethoxy)-4-nitrobenzoate as a viscous oil. This ester can be readily hydrolyzed to its acid using the procedure of Example 8.

Additional compounds were prepared by the same procedure as described in Example 5 and are listed in Table 4.

TABLE 4

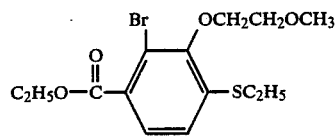

| $R^{10}$ | Physical Constant (m.p. °C.) |
|---|---|
| $CO_2H$ | 63–68 |

EXAMPLE 6

Ethyl 2-bromo-3-(2-methoxyethoxy)-4-ethylthiobenzoate

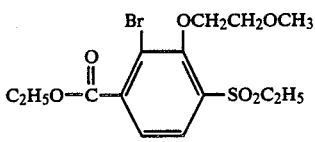

Using a procedure similar to that of Example 3, 0.1 mole of ethyl 2-bromo-3-(2-methoxyethoxy)-4-nitrobenzoate and an excess of potassium carbonate (0.2 mole) and a slight excess of ethyl mercaptan (0.125 mole) were combined in 200 mL of dimethylformamide at 0° C., under nitrogen. The reaction was stirred overnight at room temperature. Normal workup gave the desired product in essentially quantitative yield. This compound was compared to the product from Example 3 and they were identical by all spectroscopic and chromatographic comparisons.

EXAMPLE 7

Ethyl 2-bromo-3-(2-methoxyethoxy)-4-ethylsulfonyl benzoate

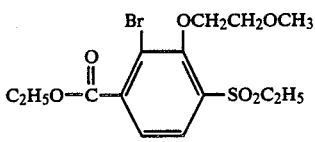

The ester, ethyl 2-bromo-3-(2-methoxyethoxy)-4-ethylthiobenzoate from Example 3 (12 g) was dissolved in 100 mL of methylene chloride and solid m-chloroperoxybenzoic acid (85% pure, 0.1 mole) was added slowly over a period of 2 hours. The crude reaction mixture was stirred overnight. The excess peracid was destroyed with sodium bisulfite (100 ml, 5%, solution). The organic layer was washed three times with base, dried, concentrated and chromatographed on silica gel ($CH_2Cl_2/(C_2H_5)_2O$) to give 8.3 grams of pure ethyl 2-bromo-3-(2-methoxyethoxy)-4-ethylsulfonylbenzoate as a viscous oil.

Additional compounds were prepared by the same procedure as described in Example 7 and are listed in Table 5.

TABLE 5

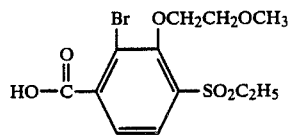

| $R^b$ | $R^{11}$ | $R^{12}$ | Physical Constant (m.p. °C.) |
|---|---|---|---|
| $C_2H_5$ | $C_2H_4OCH_3$ | $n$-$C_3H_7$ | oil |
| $C_2H_5$ | $C_2H_4OCH_3$ | $CH_3$ | oil |

EXAMPLE 8

2-bromo-3-(2-methoxyethoxy)-4-ethylsulfonylbenzoic acid

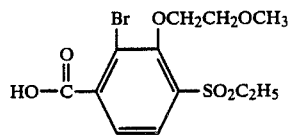

To 7.26 g (0.02 mole) of the ethyl 2-bromo-3-(2-methoxyethoxy)-4ethylsulfonylbenzoate in 50 mL of 80% methanol/water was added 1.2 g (0.03 mole) of sodium hydroxide. After stirring at room temperature overnight, 100 mL of ether was added and the organic phase was extracted three times with 50 mL of 1 N NaOH. The combined base extracts were acidified and extracted three times with methylene chloride. The methylene chloride was dried and concentrated to yield 6.6 grams of 2-bromo-3-(2-methoxyethoxy)-4-ethylsulfonylbenzoic acid as a viscous oil.

Additional compounds were prepared by the same procedure as described in Example 5 and are listed in Table 6.

TABLE 6

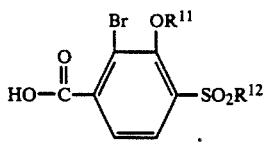

| $R^{11}$ | $R^{12}$ | Physical Constant (m.p. °C.) |
|---|---|---|
| $C_2H_4OCH_3$ | $\underline{n}$-$C_3H_7$ | 112–115 |
| $C_2H_4OCH_3$ | $CH_3$ | oil |

The other intermediate compounds can be prepared by the general method shown in FIG. II of the next page wherein $R^{20}$ is $C_1$–$C_2$ alkyl; preferably methyl; formyl; cyano; carboxy; or —$CO_2R^c$ where $R^c$ is $C_1$–$C_4$ alkyl, preferably ethyl; most preferably $R^{20}$ is —$CO_2C_2H_5$; $R^{21}$ is —$CH_2CH_2OCH_3$; —$CH_2CH_2OC_2H_5$; —$CH_2CH_2SC_2H_3$; or —$CH_2CH_2SC_2H_5$. $R^{22}$ is $C_1$–$C_4$ alkyl, preferably methyl, ethyl or n-propyl and $R^{25}$ is —$CH_2CH_2OCH_3$ or —$CH_2CH_2OC_2H_5$. $R^z$ is $C_1$–$C_4$ alkyl.

FIGURE II

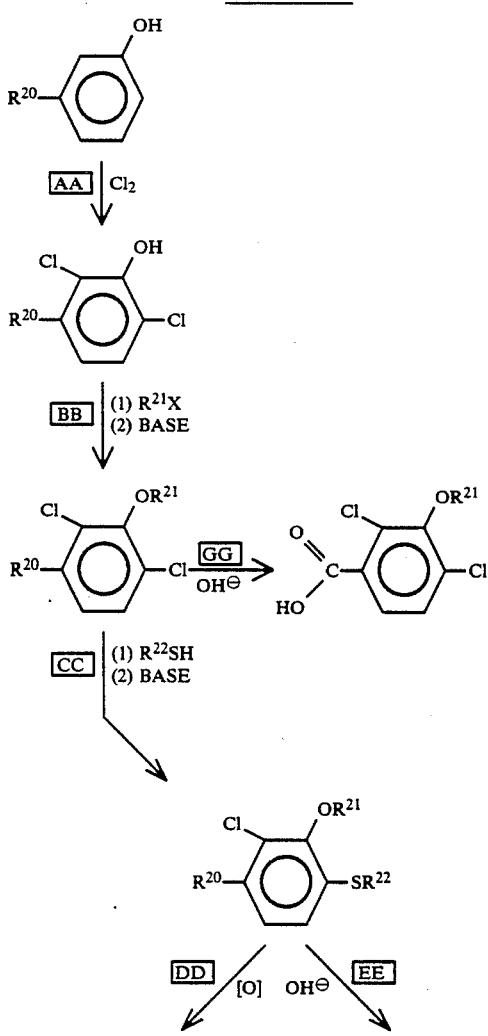

—continued FIGURE II

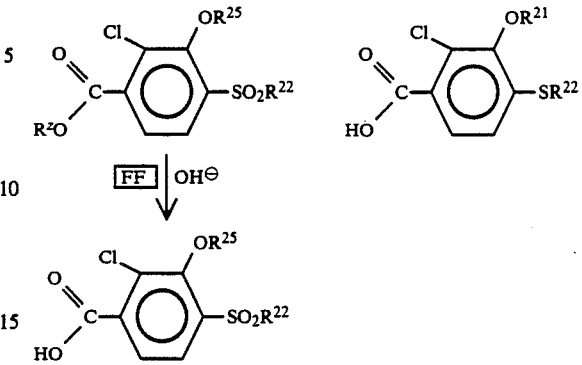

Referring to FIG. II, and particularly to Reaction Steps (AA) through (GG), consider the following:

Generally in Reaction Step (AA), a mole amount of the 3-substituted phenol is reacted with 2 moles of chlorine and a catalytic amount of a $C_1$–$C_{10}$ alkylamine, preferably tert-butylamine or diisopropylamine in a solvent such as methylene chloride, at a temperature between −70° C. to 70° C. After this reaction, the free chlorinated phenol is isolated by normal procedures.

For Reaction Step (BB), one mole of the dichloro-substituted phenol reaction product of Step (AA) is reacted with an appropriate alkylating agent such as a 2-chloroethyl ethyl ether, 2-chloroethyl methyl ether, 2-chloroethyl methyl sulfide, 2-chloroethyl ethyl sulfide or $C_1$–$C_4$ alkylchloride along with a catalytic amount of potassium iodide and a mole excess of a base such as potassium carbonate. Alkyl iodides such as methyl iodide or ethyl iodide may also be used. In these cases the catalytic potassium iodide is not needed and little or no heat is required. The reaction is run at 25° C. to 80° C. for 4 hours with agitation. The reaction product is recovered by conventional techniques.

For Reaction Step (CC), the dichloro compound from Reaction Step (BB) is reacted with an equal mole amount of a $C_1$–$C_4$ alkyl mercaptan along with a mole excess of a base such as potassium carbonate in a solvent such as dimethylformamide. The reaction is run for several hours at a temperature between 50° C. to 100° C. with stirring under an inert atmosphere such as nitrogen. The desired reaction product is recovered by conventional techniques.

For Reaction Step (DD) a mole amount of the alkyl ester of 2-chloro-4-alkylthio benzoic compound is oxidized with at least 3 moles of an oxidizing agent such as m-chloroperbenzoic acid in a suitable solvent such as methylene chloride by stirring a solution of the reactants at 20° to 100° C. The desired intermediate is recovered by conventional techniques. During this reaction step the 4-alkylthio substituent is oxidized to the corresponding alkylsulfone.

For Reaction Step (EE) a mole amount of the 2-chloro-3-substituted-4-alkylthio ester or cyano compound is hydrolyzed with a base such as sodium hydroxide to the corresponding 2-chloro-3-substituted-4-alkylthio benzoic acid. The hydrolysis is run in a solvent such as an 80 percent methanol-water mixture. The reaction can be run at 25°–100° C. with stirring. The desired product is recovered by conventional techniques.

For Reaction Step (FF) the alkyl ester of the trisubstituted benzoic acid is converted to the trisubstituted benzoic acid by the hydrolysis step taught in Reaction Step (EE).

In the alternative, the tri-substituted benzoic acid reaction product of Reaction Step (FF) can be directly prepared from the reaction product of Reaction Step (CC) by a combination hydrolysis of the 2-chloro-3-substituted-4-alkylthio ester or cyano compound to the corresponding benzoic acid and an oxidation of the 4-alkylthio substituent to the corresponding 4-alkylsulfone. The hydrolysis and oxidation steps can be jointly carried out by reacting a mole of the ester or cyano compound with at least 5 moles of sodium or calcium hypochlorite in a suitable solvent such as dioxane-water, by heating a solution of the reactants from about 25° C. to about 100 C., followed by the acidification with concentrated hydrochloric acid. Filtration of the resulting precipitate yields the desired product.

For Reaction Step (GG) the dichloro compound from Reaction Step (BB) is converted to the benzoic acid by the hydrolysis step taught in Reaction Step (EE).

The intermediate benzoic acids described herein can easily be converted to their respective acid chlorides and then to their acid cyanides, if desired, by the following two reactions. First, a mole of oxalyl chloride and a catalytic amount of dimethylformamide in a suitable solvent such as methylene chloride at a temperature of 20° to 40° C. for 1 to 4 hours is heated with a mole of the intermediate benzoic acid. The corresponding benzoic acid cyanide can easily be prepared from the benzoic acid chloride by reaction with cuprous cyanide at a temperature of 50° to 220° C. for 1 to 2 hours.

The following series of examples teach the synthesis of representative intermediate compounds of this invention. The structures of all compounds of the examples and tables were verified by nuclear magnetic resonance (NMR), infrared spectroscopy (IR) and mass spectroscopy (MS).

EXAMPLE 9

Ethyl 2,4-chloro-3-hydroxybenzoate

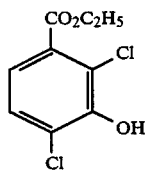

In a 3-neck, 1-liter flask equipped with a mechanical stirrer, condenser, thermometer and a diffusion tube was added a solution of 106 grams (0.64 mole) ethyl 3-hydroxybenzoate and 0.5 grams diisopropylamine in 600 ml dichloroethane at reflux. Chlorine (112 grams, 1.6 mole) was added through the diffusion tube over a period of 6 hours then let cool to room temperature. After cooling, the solution was washed with 200 mL 5% sodium bisulfite solution, then with 200 mL water, dried (MgSO4) and reduced under vacuum. Yield was 151 g of an oil. This mixture of chlorinated compounds (66% above product) can be recrystallized in ether/pentane by cooling to −20° C. to give pure ethyl 2,4-dichloro-3-hydroxybenzoate. The structure of this compound and all examples were verified by nuclear magnetic resonance (NMR), infrared spectroscopy (IR) and mass spectroscopy (MS).

Additional compounds were prepared by the same procedure as described in Example 9 and are listed in Table 7.

TABLE 7

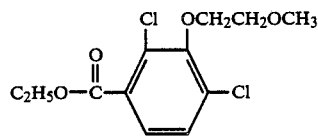

| $R^{20}$ | Yield (%) | m.p. °C. |
|---|---|---|
| $CO_2CH_3$ | 72 | 57–64 |
| $CO_2CH(CH_3)_2$ | 66 | oil |

EXAMPLE 10

Ethyl 2,4-chloro-3-(2-methoxyethoxy) benzoate

A solution of 18 g (77 millimoles, mmol) ethyl 2,4-dichloro-3-hydroxybenzoate, 22 g (3 equivalents) (eq) 2-chloroethyl methyl ether, 22 g (2 eq) potassium carbonate and ca. 0.5 g sodium iodide in 100 mL DMF was heated at 80° C. for 1.5 hours. To the cooled solution was added 400 mL ether. The organic phase was washed with 100 mL water (2 times), 100 mL 100% NaOH and 100 mL 10% HCl. Dried (MgSO4) and reduced under vacuum. The yield was 20 g (68 mole).

Additional compounds were prepared by the same procedure as described in Example 10 (except in those cases using alkyl iodide then the potassium iodide catalyst was omitted and little or no heat is required) and are listed in Table 8.

TABLE 8

| $R^{20}$ | $R^{21}$ | Physical Property | Yield (%) |
|---|---|---|---|
| $CO_2C_2H_5$ | $CH_2CH_2OCH_3$ | oil | 30 |
| $CO_2C_2H_5$ | $CH_2CH_2SCH_2H_5$ | oil | 66 |

EXAMPLE 11

Ethyl 2-chloro-3-(2-methoxyethoxy)-4-ethylthiobenzoate

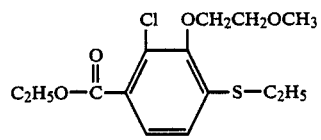

A solution of 10 g (34 mmole) ethyl 2,4-dichloro-3-(2-methoxyethoxy)benzoate, 10 g (4 eq) ethanethiol and 10 g (2 eq) potassium carbonate in 100 mL DMF was heated (approximately 100° C.) for 2 hours, then let cool overnight. Added 400 mL diethyl ether and washed with 100 mL water (two times), 100 mL 10% HCl and 100 mL 10% NaOH. Dried (MgSO₄) and reduced under vacuum. Yield 10 g (31 mmole) of an oil.

Additional compounds were prepared by the same procedure as described in Example 11 and are listed in Table 9.

TABLE 9

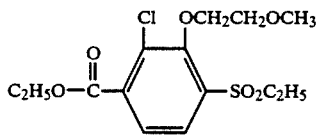

| $R^{20}$ | $R^{21}$ | $R^{22}$ | Yield (%) |
|---|---|---|---|
| CO₂C₂H₅ | CH₂CH₂OCH₃ | C₂H₅ | 46 |
| CO₂C₂H₅ | CH₂CH₂OCH₃ | n-C₃H₇ | 86 |
| CO₂C₂H₅ | H | C₂H₅ | 15 |
| CO₂CH₃ | H | C₂H₅ | — |
| CO₂CH₃ | CH₂CH₂OCH₃ | C₂H₅ | 90 |
| CO₂CH₃ | CH₂CH₂OCH₃ | n-C₃H₇ | 87 |
| CO₂CH₃ | CH₂CH₂OCH₃ | CH₃ | 65 |

EXAMPLE 12

Ethyl 2-chloro-3-(2-methoxyethoxy)-4-ethylsulfonyl benzoate

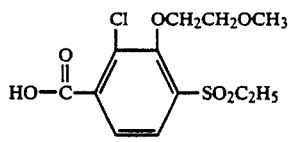

The ester, ethyl 2-chloro-3-(2-methoxyethoxy)-4-ethylthiobenzoate from Example 3 (10 g) was dissolved in 100 mL of methylene chloride and cooled with an ice bath. Next 18 g solid m-chloroperoxybenzoic acid (85% pure, 2.2 equivalents) was allowed in portions over a period of 2 hours. The crude reaction mixture was allowed to warm to room temperature. After 1 hour at room temperature the excess peracid was destroyed with sodium bisulfite (100 mL 5% solution). The organic layer was washed two times with 5% sodium hydroxide (100%) and stripped under vacuum to give 11.3 grams of pure ethyl 2-chloro-3-(2-methoxyethoxy)-4-ethylsulfonylbenzoate as a viscous oil.

Additional compounds were prepared by the same procedure as described in Example 12 and are listed in Table 10.

TABLE 10

| $R^a$ | $R^{25}$ | $R^{22}$ | Yield (%) |
|---|---|---|---|
| C₂H₅ | C₂H₄OCH₃ | C₂H₅ | 72 |
| C₂H₅ | C₂H₄OCH₃ | n-C₃H₇ | 98 |
| CH₃ | C₂H₄OCH₃ | C₂H₅ | 100 |
| CH₃ | C₂H₄OCH₃ | n-C₃H₇ | 97 |

TABLE 10-continued

| $R^a$ | $R^{25}$ | $R^{22}$ | Yield (%) |
|---|---|---|---|
| CH₃ | CH₂CH₂OCH₃ | CH₃ | 87 |

EXAMPLE 13

2-chloro-3-(2-methoxyethoxy)-4-ethylsulfonylbenzoic acid

To 11.3 g (0.03 mole) of the ethyl 2-chloro-3-(2-methoxyethoxy)-4-ethylsulfonylbenzoate in 100 mL of 96% ethanol was added dropwise 16 mL (1.2 eq) of 10% sodium hydroxide. After stirring at room temperature for 4 hours, 100 mL of diethyl ether was added and the organic phase was extracted with 50 mL of 5% NaOH. The aqueous phase was acidified with 10% HCl and extracted two times with 50 mL chloroform. The organic phase was dried with MgSO₄ and concentrated under vacuum to yield 8.8 grams of 2-chloro-3-(2-methoxyethoxy)4-ethylsulfonylbenzoic acid as a viscous oil.

Additional compounds were prepared by the same procedure as described in Example 13 and are listed in Table 11.

TABLE 11

| $R^{25}$ | $R^{22}$ | Yield (%) |
|---|---|---|
| CH₂CH₂OCH₃ | n-C₃H₇ | 77 |
| CH₂CH₂OCH₃ | CH₃ | 80 |

EXAMPLE 14

2-Chloro-3-(2-methoxyethoxy)-4-ethylthio benzoic acid

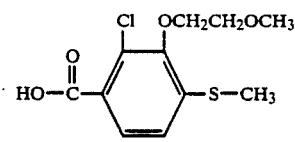

Three grams (8.2 mmol) ethyl 2-chloro-3-(2-methoxyethoxy)-4-propanethiobenzoate was dissolved in 20 mL 96% ethyl alcohol. To this was added 3.9 mL 10% sodium hydroxide in water. After stirring 4 hours at room temperature, 100 mL of diethyl ether was added to the solution. The solution was extracted twice with 50 mL 5% sodium hydroxide solution. The combined caustic extracts were acidified with 10% hydrochloric acid and extracted twice with 50 mL portions of chloroform. The chloroform extracts were dried over magnesium sulfate and the chloroform removed in vacuo to afford the free acid (2.0 g, 72%) as a soft solid.

Additional compounds were prepared by the same procedure as described in Example 14 and are listed in Table 12.

TABLE 12

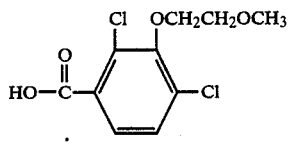

| $R^{21}$ | $R^{22}$ | Yield (%) |
|---|---|---|
| $CH_2CH_2OCH_3$ | $C_2H_5$ | 72 |

EXAMPLE 15
2,4-Dichloro-3-(2-methoxyethoxy) benzoic acid

Sixteen grams (41 mmol) ethyl 2,4-dichloro-3-(2-methoxyethoxy)benzoate was dissolved in 100 mL of 96% ethanol. To this was added, in portions, 18 mL (ca 1.1 equivalents) 10% sodium hydroxide. After stirring 4 hours at room temperature, 250 mL diethyl ether was added to the solution. The solution was extracted twice with 50 mL 5% sodium hydroxide. The combined caustic extracts were acidified with a 10% hydrochloric acid solution and extracted twice with 75 mL portions of chloroform. The chloroform extracts were dried (magnesium sulfate) and the chloroform removed in vacuo to afford the free acid (12.8 g, 79%) as a white solid.

Additional compounds were prepared by the same procedure as described in Example 15 and are listed in Table 13.

TABLE 13

| $R^{21}$ | Yield (%) |
|---|---|
| $CH_2CH_2SC_2H_5$ | 100 |

The above-described benzoic acids can be readily converted to their acid chlorides using oxalyl chloride and a catalytic amount of dimethylformamide. These acid chlorides can be reacted with the above-described 1,3-cyclohexanedione to prepare the above-described herbicidal 2,3,4-trisubstituted benzoyl-1,3-cyclohexanediones according to the two-step reaction previously described.

The following example teaches the synthesis of a representative 1,3-cyclohexanediones.

EXAMPLE 16 4-methylthiocyclohexane-1,3-dione

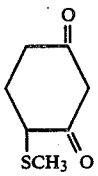

1-(Methylthio)-2-propanone [25 grams (g), 0.24 mole], ethyl acrylate (24 g, 0.24 mol), and benzyltrismethylammonium methoxide [2 mL of wt % solution in methanol] were dissolved in toluene (100 mL). To the solution was then added a solution of sodium methoxide (77.8 g of 25 wt % in methanol, 0.36 mol) dropwise at a rate as to maintain the temperature below 35° C. After stirring an additional 2 hours at room temperature, the reaction mixture was poured into 200 mL of ice water and extracted with 100 mL of ether. The aqueous phase was acidified with 2 N hydrochloric acid and extracted with ether. The ether layer was dried over magnesium sulfate, filtered, and concentrated under vacuum to afford 23.1 g of an oil. The oil was dissolved in benzene (100 mL) and the desired product slowly deposited out of the solution as waxy crystals (9.8 g).

The following example teaches the synthesis of a representative 2-(2', 3',4'-trisubstituted)-1,3-cyclohexanedione.

EXAMPLE 17
2-[2'Bromo-3'-(2-methoxyethoxy)-4'ethylsulfonyl)benzoyl]-1,3-cyclohexanedione

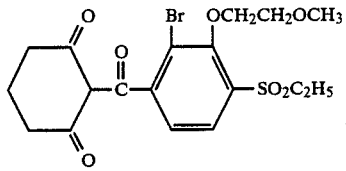

2-Bromo-3-(2-methoxyethoxy)-4-ethylsulfonyl benzoic acid (6.1 g, 0.018 mol) was diluted in 50 mL of methylene chloride and 2 drops of DMF were added, followed by the slow addition of oxalyl chloride (3.81 g, 0.03 mol). After the addition was complete, the solution was refluxed for 1 hour, cooled and concentrated under vacuum. The crude acid chloride was diluted in 25 mL of methylene chloride and 2.24 g (0.02 mol) of 1,3-cyclohexanedione was added, followed by an excess of triethylamine (4.0 g). After stirring overnight, the organic layer was washed three times with dilute (1 N) hydrochloric acid, dried and concentrated. The crude enol ester was dissolved in 25 mL of acetonitrile and ten drops of acetone cyanohydrin and 4 mL of triethylamine were added and this reaction mixture was stirred at room temperature for 48 hours. The organic phase was washed three times with 1 N hydrochloric acid and then extracted with base. The base extracts were combined and acidified and extracted three times with 50 mL of methylene chloride. The methylene chloride extracts were dried, concentrated and chromatographed on silica gel using ether/methylene chloride/acetic acid to give 3.96 g of pure 2-[2'-bromo-3'-(2-methoxyethoxy)-4'-ethylsulfonylbenzoyl]-1,3-cyclohexanedione.

The following is a table of certain selected compounds that are preparable according to the procedure described hereto. Compound numbers are assigned to each compound and are used throughout the remainder of the application.

lacunosa), hemp sesbania (SESB) (*Sesbania exaltata*), velvetleaf (VL) (*Abutilon theophrasti*), sicklepod (SP) (*Cassia obtusifolia*), yellow nutsedge (YNG) (*Cyperus esculentus*) and cocklebur (CB) (*Xanthium sp.*). Apple seeds are planted to give about 20 to 40 seedlings per

TABLE 14

| Comp. No. | R | $R^1$ | $R^2$ | $R^3$ | $R^4$ | $R^5$ | $R^6$ | $R^7$ | $R^8$ | X | m.p. °C |
|---|---|---|---|---|---|---|---|---|---|---|---|
| 1 | Br | H | H | H | H | H | H | $CH_3$ | Br | O | oil |
| 2 | Br | $CH_3$ | $CH_3$ | H | H | H | H | $CH_3$ | Br | O | oil |
| 3 | Br | $CH_3$ | $CH_3$ | —O— | | $CH_3$ | $CH_3$ | $CH_3$ | Br | O | oil |
| 4 | Br | $CH_3$ | $CH_3$ | H | H | H | H | $C_2H_5$ | Br | O | 97-103 |
| 5 | Br | H | H | H | H | H | H | $C_2H_5$ | Br | O | oil |
| 6 | Br | $CH_3$ | $CH_3$ | —O— | | $CH_3$ | $CH_3$ | $C_2H_5$ | Br | O | oil |
| 7 | Br | H | H | H | H | H | H | $CH_3$ | Br | S | oil |
| 8 | Br | $CH_3$ | $CH_3$ | H | H | H | H | $CH_3$ | $n\text{-}C_3H_7SO_2$ | O | oil |
| 9 | Br | $CH_3$ | $CH_3$ | —O— | | $CH_3$ | $CH_3$ | $CH_3$ | $n\text{-}C_3H_7SO_2$ | O | oil |
| 10 | Br | $CH_3$ | $CH_3$ | —O— | | $CH_3$ | $CH_3$ | $CH_3$ | $C_2H_5SO_2$ | O | oil |
| 11 | Br | $CH_3$ | $CH_3$ | H | H | H | H | $CH_3$ | $C_2H_5SO_2$ | O | oil |
| 12 | Br | H | H | H | H | H | H | $CH_3$ | $C_2H_5SO_2$ | O | oil |
| 13 | Br | $CH_3$ | $CH_3$ | H | —OH | $CH_3$ | $CH_3$ | $CH_3$ | Br | O | oil |
| 14 | Br | $CH_3$ | $CH_3$ | H | H | $CH_3$ | $CH_3$ | $CH_3$ | Br | O | oil |
| 15 | Br | $CH_3$ | $CH_3$ | H | H | $CH_3$ | $CH_3S$ | $CH_3$ | Br | O | oil |
| 16 | Br | $CH_3$ | $CH_3$ | H | H | $CH_3$ | $CH_3SO_2$ | $CH_3$ | Br | O | oil |
| 17 | Br | H | H | H | H | H | H | $CH_3$ | $n\text{-}C_3H_7SO_2$ | O | 118-112 |
| 18 | Br | H | H | H | H | H | H | $CH_3$ | $CH_3SO_2$ | O | 87-90 |
| 19 | Br | $CH_3$ | $CH_3$ | H | H | H | H | $CH_3$ | $CH_3SO_2$ | O | oil |
| 20 | Br | $CH_3$ | $CH_3$ | —O— | | $CH_3$ | $CH_3$ | $CH_3$ | $CH_3SO_2$ | O | oil |
| 21 | Cl | H | H | H | H | H | H | $CH_3$ | $C_2H_5SO_2$ | O | oil |
| 22 | Cl | $CH_3$ | $CH_3$ | H | H | H | H | $CH_3$ | $C_2H_5SO_2$ | O | oil |
| 23 | Cl | H | H | H | H | H | H | $CH_3$ | Cl | O | oil |
| 24 | Cl | $CH_3$ | $CH_3$ | H | H | H | H | $CH_3$ | Cl | O | oil |
| 25 | Cl | $CH_3$ | $CH_3$ | H | OH | $CH_3$ | $CH_3$ | $CH_3$ | Cl | O | glassy solid |
| 26 | Cl | $CH_3$ | $CH_3$ | H | H | $CH_3$ | H | $CH_3$ | Cl | O | glassy solid |
| 27 | Cl | $CH_3$ | $CH_3$ | —O— | | $CH_3$ | $CH_3$ | $CH_3$ | Cl | O | oil |
| 28 | Cl | H | H | H | H | H | H | $CH_3$ | $n\text{-}C_3H_7SO_2$ | O | oil |
| 29 | Cl | $CH_3$ | $CH_3$ | H | H | H | H | $CH_3$ | $n\text{-}C_3H_7SO_2$ | O | oil |
| 30 | Cl | H | H | H | H | H | H | $CH_3$ | $n\text{-}C_3H_7S$ | O | oil |
| 31 | Cl | H | H | H | H | H | H | $C_2H_5$ | Cl | S | oil |
| 32 | Cl | $CH_3$ | $CH_3$ | H | H | H | H | $C_2H_5$ | Cl | S | oil |
| 33 | Br | $CH_3$ | $CH_3$ | —O— | | $CH_3$ | $CH_3$ | $CH_3$ | Br | S | oil |
| 34 | Br | H | H | $CH_3$ | H | H | H | $CH_3$ | $C_2H_5SO_2$ | O | oil |
| 35 | Br | H | H | H | H | H | H | $CH_3$ | $NO_2$ | O | oil |
| 36 | Cl | H | H | $CH_3$ | H | H | H | $CH_3$ | $n\text{-}C_3H_7SO_2$ | O | oil |
| 37 | Cl | H | H | $CH_3$ | H | H | H | $CH_3$ | $C_2H_5SO_2$ | O | oil |
| 38 | Cl | H | H | H | H | H | H | $CH_3$ | $CH_3SO_2$ | O | oil |

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence multi-weed herbicide test.

On the day preceding treatment, seeds of twelve different weed species are planted in loamy sand soil in individual rows using one species per row across the width of a flat. The weeds used are green foxtail (FT) (*Setaria viridis*), annual ryegrass (ARG) (*Lolium multiflorum*), watergrass (WG) (*Echinochloa crusgalli*), shattercane (SHC) (*Sorghum bicolor*), wild oat (WO) (*Avena fatua*), broadleaf signalgrass (BSG) (*Brachiaria platyphylla*), annual morningglory (AMG) (*Ipomoea* row, after emergence, depending upon the size of the plants.

Using an analytical balance, 37.5 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 40 gallons per acre (748 L/ha). The application rate is /14 lb/acre (0.28 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the test are shown in the following Table 15.

Also, watering of the treated flats is confined to the soil surface and not to the foliage of the sprouted plants.

Post-Emergence Multi-Weed Herbicide Test:

This test is conducted in an identical manner to the testing procedure for the post-emergence herbicide test, except the seeds of the twelve weed species used in the pre-emergence multi-weed herbicide test were used and

TABLE 15

Pre-Emergence Herbicidal Activity
Application Rate - 0.25 lb/A

| Cmpd. No. | FT | ARG | WG | SHC | WO | BSG | AMG | SESB | VL | SP | YNS | CB |
|---|---|---|---|---|---|---|---|---|---|---|---|---|
| 1 | 100 | 70 | 100 | 95 | 85 | 95 | 35 | 100 | 100 | 80 | 95 | 100 |
| 2 | 100 | 85 | 100 | 95 | 100 | 65 | 75 | 100 | 100 | 15 | 75 | 80 |
| 3 | 100 | 100 | 100 | 100 | 100 | 85 | 100 | 100 | 100 | 95 | 75 | 100 |
| 4 | | 0 | 100 | 100 | 0 | 90 | 0 | 80 | 100 | 0 | 10 | 0 |
| 5 | 85 | 5 | 95 | 80 | 25 | 95 | 10 | 80 | 95 | 15 | 30 | 20 |
| 6 | 95 | 0 | 5 | 90 | 0 | 60 | 20 | 50 | 75 | 0 | 0 | 0 |
| 7 | 100 | 80 | 90 | 100 | 90 | 100 | 85 | 100 | 100 | 95 | | 50 |
| 8 | 100 | 0 | 80 | 90 | 0 | 90 | 90 | 90 | 100 | 10 | 0 | 50 |
| 9 | 10 | 0 | 20 | 50 | 0 | 30 | 95 | 100 | 100 | 10 | 0 | 50 |
| 10 | 5 | 0 | 85 | 80 | 50 | 0 | 98 | 98 | 100 | 10 | 0 | 50 |
| 11 | 95 | 10 | 100 | 100 | 50 | 90 | 100 | 100 | 100 | 10 | 30 | 40 |
| 12 | 100 | 5 | 100 | 100 | 80 | 100 | 100 | 98 | 100 | 50 | 95 | 70 |
| 13 | 100 | 95 | | | | | 100 | | | | | |
| 14 | | | 50 | | 0 | 10 | | | 85 | 0 | 0 | 0 |
| 15 | | | 80 | | 20 | 25 | | | 85 | 10 | 30 | 0 |
| 16 | | | 60 | | 15 | 50 | | | 100 | 0 | 20 | — |
| 17 | 100 | 90 | 100 | 100 | 100 | 100 | 100 | 100 | 100 | 95 | 90 | 90 |
| 18 | 100 | 85 | 100 | 100 | 95 | 100 | 100 | 100 | 100 | 20 | 90 | 60 |
| 19 | | | 100 | | 100 | 100 | | | 100 | 80 | 85 | — |
| 20 | 5 | 89 | 70 | | | | 95 | | | | | |
| 21 | 100 | 80 | 100 | 100 | 100 | 100 | 100 | 100 | 100 | 100 | 95 | 100 |
| 22 | | | 100 | | 100 | 100 | | | 100 | 60 | 75 | — |
| 23 | | | 100 | | 90 | 85 | | | 100 | 90 | 95 | 100 |
| 24 | | | 100 | | 50 | 90 | | | 100 | 50 | 80 | — |
| 25 | 100 | 95 | | | | | 90 | | | | | |
| 26 | | | 85 | | 50 | 10 | | | 100 | 10 | 0 | — |
| 27 | | | 100 | | 20 | 75 | | | 100 | 40 | 10 | — |
| 28 | 100 | 80 | 100 | 100 | 100 | 100 | 100 | 100 | 100 | 100 | 95 | 100 |
| 29 | | | 100 | | 90 | 90 | | | 100 | 70 | 95 | 100 |
| 30 | | | 100 | | 40 | 90 | | | 100 | 60 | 90 | 50 |
| 31* | 100 | | 100 | | 100 | | 100 | | 100 | | 80 | |
| 32 | 100 | | 100 | | 100 | 100 | | | 100 | 100 | | |
| 33 | 100 | | 100 | | 100 | ·100 | 100 | | 100 | 80 | | |
| 34 | 100 | | 100 | | 100 | 100 | | | 100 | 50 | | 100 |

A dash (—) indicates that no rating was obtained.
A blank space indicates that the weed species was not in the test.
*Tested at 1.14 kg/ha.

Post-Emergence Multi-Weed Herbicide Test:

This test is conducted in an identical manner to the testing procedure for the pre-emergence multi-weed herbicide test, except the seeds of the twelve different weed species are planted 10–12 days before treatment.

the seeds were planted 10–12 days before treatment. Also, watering of the treated flats is confined to the soil surface and not to the foliage of the sprouted plants.

The results of the post-emergence multi-weed herbicide test are reported in Table 16.

TABLE 16

Post-Emergence Multi-Weed Herbicidal Activity
Application Rate - 0.28 kg/ha

| Cmpd. No. | FT | ARG | WG | SHC | WO | BSG | AMG | SESB | VL | SP | YNS | CB |
|---|---|---|---|---|---|---|---|---|---|---|---|---|
| 1 | 60 | 25 | 100 | 35 | 100 | 65 | 100 | 100 | 100 | 98 | 75 | 100 |
| 2 | 100 | 50 | 100 | 90 | 100 | 100 | 100 | 85 | 75 | 40 | 40 | 50 |
| 3 | 100 | 50 | 100 | 95 | 75 | 100 | 95 | 100 | 100 | 25 | 40 | 100 |
| 4 | 60 | 5 | 90 | 85 | 10 | 75 | 100 | 95 | 100 | 25 | 70 | 95 |
| 5 | 90 | 0 | 90 | 50 | 0 | 80 | 100 | 100 | 100 | 80 | 35 | 100 |
| 6 | 90 | 0 | 30 | 35 | 0 | 35 | 60 | 100 | 90 | 30 | 0 | — |
| 7 | 10 | 85 | 90 | 90 | 90 | 100 | 95 | 100 | 100 | 90 | | 95 |
| 8 | — | 0 | 80 | 60 | 0 | 85 | 85 | 100 | 100 | 0 | 0 | 100 |
| 9 | — | 0 | 15 | 0 | 0 | 0 | 90 | 90 | 100 | 0 | 0 | 100 |
| 10 | 0 | 0 | 90 | 10 | 80 | 30 | 100 | 100 | 100. | 10 | 5 | 95 |
| 11 | 95 | 10 | 90 | 95 | 80 | 100 | 100 | 100 | 100 | 5 | 25 | 95 |
| 12 | 90 | 0 | 90 | 95 | 85 | 100 | 100 | 100 | 100 | 40 | 80 | 95 |
| 13 | 40 | 85 | | | | | 70 | | | | | |
| 14 | | | 60 | | 70 | 40 | | | | 25 | 20 | 20 | 50 |
| 15 | | | 80 | | 50 | 50 | | | | 25 | 10 | 0 | 40 |

TABLE 16-continued

Post-Emergence Multi-Weed Herbicidal Activity
Application Rate - 0.28 kg/ha

| Cmpd. No. | FT | ARG | WG | SHC | WO | BSG | AMG | SESB | VL | SP | YNS | CB |
|---|---|---|---|---|---|---|---|---|---|---|---|---|
| 16 | | | 70 | | 30 | 40 | | | 40 | 20 | 10 | 40 |
| 17 | 98 | 40 | 98 | 100 | 100 | 100 | 100 | — | 100 | 100 | 90 | 95 |
| 18 | 100 | 20 | 100 | 100 | 95 | 100 | 100 | — | 100 | 85 | 95 | 95 |
| 19 | | | 90 | | 100 | 90 | | | 100 | 50 | 70 | — |
| 20 | 0 | 54 | | | | | 95 | | | | | |
| 21 | 100 | 90 | | | | | 100 | | | | | |
| 22 | | | 85 | | 90 | 85 | | | 95 | 50 | 75 | 85 |
| 23 | | | 85 | | 90 | 90 | | | 100 | 70 | 90 | 85 |
| 24 | | | 90 | | 90 | 85 | | | 100 | 60 | 75 | — |
| 25 | 100 | 92 | | | | | 85 | | | | | |
| 26 | | | 85 | | 85 | 30 | | | 85 | 50 | 20 | 85 |
| 27 | | | 85 | | 0 | 80 | | | 85 | 25 | 0 | 85 |
| 28 | 100 | 89 | | | | | 100 | | | | | |
| 29 | | | 95 | | 80 | 85 | | | 100 | 40 | 10 | 85 |
| 30 | | | 90 | | 40 | 85 | | | 100 | 50 | 50 | — |
| 31* | 100 | | 100 | | 100 | | 100 | | 100 | | 80 | |
| 32 | 100 | | 95 | | 100 | 100 | | | 100 | 90 | | 85 |
| 33 | 90 | | 80 | | 80 | 100 | 80 | | 100 | 50 | | 60 |
| 34 | 100 | | 95 | | 95 | 100 | | | 100 | 85 | | 90 |

A dash (—) indicates that no rating as obtained.
A blank indicates that the weed species was not in the test.
*Tested at 1.14 kg/ha.

The compounds of the present invention are useful as herbicides and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 10 pounds per acre, preferably from about 0.1 to about 4 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water, or other dispersant, and may consist entirely of the active compound with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such heavy aromatic naphthas, kerosene or other petroleum fractions, or vegetable oils; and/or stickers such as destrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of which are available in commerce. The surface-active agent, When used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formations for herbicidal applications include sample solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power dusters, boom and hand sprayers and spray dusters. The compositions can also be applied from airplanes as a dust or a spray because they are effective in very low dosages. In order to modify or control growth of germinating seeds or enlarging seedlings, as a typical example, the dust and liquid compositions are applied to the soil according to conventional methods and are distributed in the soil to a depth of at least ½ inch below the soil surface. It is not necessary that the phototoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

When salts are used as the active ingredient in the herbicidal compositions of this invention it is recommended to use salts that are agriculturally acceptable.

The phytotoxic compositions of this invention can also contain other additives, for example, fertilizers, other herbicides and other pesticides, used as adjuvant or in combination with any of the above-described adjuvants. Fertilizers useful in combination with the active ingredients include, for example, ammonium nitrate, urea and superphosphate.

The herbicidal compounds of this invention can be used in combination with other herbicidal compounds for broader spectrum control of undesirable vegetation. Examples of other herbicidal compounds are as follows:

1. ANILIDES

Alachlor—2-chloro-2',6'-diethyl-N-(methoxymethyl)acetanilide
Metolachlor—2-chloro-N-(2-ethyl -6-methylphenyl)-N-(2-methoxy-1-methylethyl)acetamide
Propanil—N-(3,4-dichlorophenyl) propionanilide

2. TRIAZINES

Atrazine—2-chloro-4-(ethylamino)-6-(isopropylamino-s-triazine
Cyanazine—2-chloro-4-(1-cyano-1-methylethylamino)-6-ethylamino-s-triazine
Metribuzin—4-amino-6-tert-butyl-3-(methylthio)-1,2,4-triazin-5(4H)-one

3. THIOCARBAMATES

Molinate—S-ethyl hexahydro-1H-azepine-1-carbothioate
Butylate—S-ethyl diisobutylthiocarbamate

4. UREAS

Monuron—3-(p-chlorophenyl)-1,1-dimethylurea
Linuron—3-(3,4-dichlorophenyl)-1-methoxy-1-methylurea

5. TOLUIDINES

Trifluralin—α,α,α-trifluoro-2,6dinitro-N,N-dipropyl-p-toluidine
Pendimethalin—N-(1-ethylpropyl)-3,4-dimethyl-2,6-dinitrobenzenamine

6. HORMONES 2,4-D—(2,4-dichlorophenoxy) acetic acid
MCPA—(2-methyl-4-chlorophenoxy) acetic acid

7. DIAZINES

| General Formula with Ranges | | Specific Formula | |
| --- | --- | --- | --- |
| EMULSIFIABLE CONCENTRATE FORMULATIONS | | | |
| Herbicidal compound | 5–55 | herbicidal compound | 54 |
| surfactant(s) | 5–25 | proprietary blend of oil- | 10 |
| solvent(s) | 20–90 | soluble sulfonates and | |
| | 100% | polyoxyethylene ethers | |
| | | polar solvent | 27 |
| | | petroleum hydrocarbon | 9 |
| | | 100% | |
| WETTABLE POWDER FORMULATIONS | | | |
| herbicidal compound | 3–90 | herbicidal compound | 80 |
| wetting agent | 0.5–2 | sodium dialkyl naphthalene | 0.5 |
| dispersing agent | 1–8 | sulfonate | |
| diluent(s) | 8.5–87 | sodium lignosulfonate | 7 |
| | 100% | attapulgite clay | 12.5 |
| | | | 100% |
| EXTRUDED GRANULAR FORMULATIONS | | | |
| herbicidal compound | 1–20 | herbicidal compound | 10 |
| binding agent | 0–10 | lignin sulfonate | 5 |
| diluent(s) | 70–99 | calcium carbonate | 85 |
| | 100% | | 100% |
| FLOWABLE FORMULATIONS | | | |
| herbicidal compound | 20–70 | herbicidal compound | 45 |
| surfactant(s) | 1–10 | polyoxyethylene ether | 5 |
| suspending agent(s) | 0.05–1 | attagel | 0.05 |
| antifreeze agent | 1–10 | propylene glycol | 10 |
| antimicrobial agent | 1–10 | BIT | 0.03 |
| antifoam agent | 0.1–1 | silicone defoamer | 0.02 |
| solvent | 7.95–77.85 | water | 39.9 |
| | 100% | | 100% |

Bentazon—3-isopropyl -1H-2,3,1-benzothiadiazin-4(3H)-one 2,2-dioxide
Oxadiazon—2-tert-butyl-4-(2,4-dichloro-5-isopropoxyphenyl)-Δ²-1,3,4-oxadiazolin-5-one

8. DIPHENYL ETHERS

Acifluorfen—sodium 5-[2-chloro-4-(trifluoromethyl)-phenoxy]-2-nitrobenzoate
Fluazifop-butyl—(±)-butyl 2-[4[(5-(trifluoromethyl)-2-pyridinyl)-oxy]phenoxy]propanoate
Chlomathoxynil—2,4-dichlorophenyl 3-methoxy-4-nitrophenyl ether

9. IMIDAZOLINONES

Imazaguin—2-(4,5-dihydro-4-methyl-4-(1-methylethyl)-5-oxo-1H-imidazol-2yl)-3-quinoline carboxylic acid

10. SULFONYL UREAS

Bensulfuron methyl—2-(((((4,6-dimethoxypyrimidin-2-yl)-amino)-carbonyl)amino)sulfonyl-1)methyl) benzoate
Chlorimuron ethyl—ethyl 2-((((((4-chloro-6-methoxypyrimidin-2-yl)-amino)carbonyl)amino)sulfonyl)-benzoate

11. MISCELLANEOUS COMPOUNDS

Dimethazone—2-(2-chlorophenyl)methyl-4,4-dimethyl-3-isoxazolidinone
Norflurazon—4-chloro-5-(methylamino)-2-(α,α,α-trifluoro-m-tolyl)-3-(2H)-pyridazinone
Dalapon—2,2-dichloropropionic acid
Glyphosate—isopropyl amine salt of N-(phosphonomethyl)glycine
Fenoxaprop-ethyl—(+)-ethyl-2,4-((6-chloro-2-benzoxazolyloxy)phenoxy) propanoate

What is claimed is:

1. A compound having the structural formula

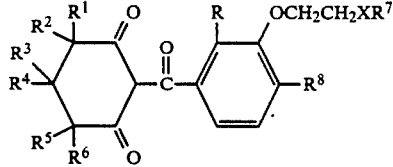

wherein
X is oxygen or sulfur;
R is chlorine or bromine;
$R^1$ is hydrogen or $C_1$-$C_4$ alkyl;
$R^2$ is hydrogen or $C_1$-$C_4$ alkyl;
$R^3$ is hydrogen or $C_1$-$C_4$ alkyl;
$R^4$ is hydroxy, hydrogen or $C_1$-$C_4$ alkyl; or
$R^3$ and $R^4$ together are carbonyl (=O) with the proviso that $R^1$, $R^2$, $R^5$ and $R^6$ are all $C_1$-$C_4$ alkyl;
$R^5$ is hydrogen or $C_1$-$C_4$ alkyl;
$R^6$ is hydrogen, $C_1$-$C_4$ alkyl, $C_1$-$C_4$ alkylthio or $C_1$-$C_4$ alkylsulfonyl;
$R^7$ is methyl or ethyl; and
$R^8$ is (1) halogen; (2) nitro; or (3) $R^bSO_n$— wherein n is the integer 0 or 2; and $R^b$ is (a) $C_1$-$C_3$ alkyl; and its salts.

2. A compound of claim 1 wherein R is chlorine or bromine; $R^1$ is hydrogen or methyl; $R^2$ is hydrogen or methyl; $R^3$ is hydrogen or methyl; $R^4$ is hydrogen or methyl or $R^3$ and $R^4$ together are carbonyl with the proviso that $R^1$, $R^2$, $R^5$ and $R^6$ are all methyl; $R^5$ is hydrogen or methyl; $R^6$ is hydrogen, methyl, methylthio or methylsulfonyl; $R^7$ is methyl or ethyl; $R^8$ is hydrogen, chlorine, bromine, nitro or $R^bSO_2$ wherein $R^b$ is $C_1$-$C_3$ alkyl.

3. The compound of claim 2 wherein R is bromine, $R^1$ is methyl, $R^2$ is methyl, $R^3$ is hydrogen, $R^4$ is hydrogen, $R^5$ is hydrogen, $R^6$ is hydrogen, $R^7$ is methyl, $R^8$ is bromine and X is oxygen.

4. The compound of claim 2 wherein R is bromine, $R^1$ is hydrogen, $R^2$ is hydrogen, $R^3$ is hydrogen, $R^4$ is hydrogen, $R^5$ is hydrogen, $R^6$ is hydrogen, $R^7$ is methyl, $R^8$ is n—$C_3H_7SO_2$ and X is oxygen.

5. The compound of claim 2 wherein R is chlorine, $R^1$ is hydrogen, $R^2$ is hydrogen, $R^3$ is hydrogen, $R^4$ is hydrogen, $R^5$ is hydrogen, $R^6$ is hydrogen, $R^7$ is methyl, $R^8$ is $C_2H_5SO_2$ and X is oxygen.

6. The compound of claim 2 wherein R is chlorine, $R^1$ is hydrogen, $R^2$ is hydrogen, $R^3$ is hydrogen, $R^4$ is hydrogen, $R^5$ is hydrogen, $R^6$ is hydrogen, $R^7$ is methyl, $R^8$ is n-$C_3H_7SO_2$ and X is oxygen.

7. The compound of claim 2 wherein R is bromine, $R^1$ is methyl, $R^2$ is methyl, $R^3$ and $R^4$ together are carbonyl, $R^5$ is methyl, $R^6$ is methyl, $R^7$ is methyl, $R^8$ is bromine and X is sulfur.

8. The compound of claim 2 wherein R is bromine, $R^1$ is hydrogen, $R^2$ is hydrogen, $R^3$ is methyl, $R^4$ is hydrogen, $R^5$ is hydrogen, $R^6$ is hydrogen, $R^7$ is methyl, $R^8$ is $C_2H_5SO_2$ and X is oxygen.

9. The method of controlling undesirable vegetation comprising applying to the area where control is desired, an herbicidally effective amount of a compound having the structural formula

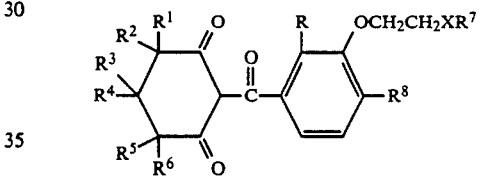

wherein
X is oxygen or sulfur;
R is chlorine or bromine;
$R^1$ is hydrogen or $C_1$-$C_4$ alkyl;
$R^2$ is hydrogen or $C_1$-$C_4$ alkyl;
$R^3$ is hydrogen or $C_1$-$C_4$ alkyl;
$R^4$ hydroxy, hydrogen or $c_1$-$C_4$ alkyl; or
$R^3$ and $R^4$ together are carbonyl (=O) with the proviso that $R^1$, $R^2$, $R^5$ and $R^6$ are all $C_1$-$c_4$ alkyl;
$R^5$ is hydrogen or $C_1$-$C_4$ alkyl;
$R^6$ is hydrogen, $C_1$-$C_4$ alkyl, $C_1$-$C_4$ alkylthio or $C_1$-$C_4$ alkylsulfonyl;
$R^7$ is methyl or ethyl; and
$R^8$ is (1) halogen; (2) nitro; or (3) $R^bSO_n$— wherein n is the integer 0 or 2; and $R^b$ is (a) $C_1$-$C_3$ alkyl; and its salts.

10. The method of claim 9 wherein R is chlorine or bromine; $R^1$ is hydrogen or methyl; $R^2$ is hydrogen or methyl; $R^3$ is hydrogen or methyl; $R^4$ is hydrogen or methyl or $R^3$ and $R^4$ together are carbonyl with the proviso that $R^1$, $R^2$, $R^5$ and $R^6$ are all methyl; $R^5$ is hydrogen or methyl; $R^6$ is hydrogen, methyl, methylthio or methylsulfonyl; $R^7$ is methyl or ethyl; $R^8$ is hydrogen, chlorine, bromine, nitro or $R^bSO_2$— wherein $R^b$ is $C_1$-$C_3$ alkyl.

11. The method of claim 10 wherein $R^1$ is methyl, $R^2$ is methyl, $R^3$ is hydrogen, $R^4$ is hydrogen, $R^5$ is hydrogen, $R^6$ is hydrogen, $R^7$ is methyl, $R^8$ is bromine and X is oxygen.

12. The method of claim 10 wherein R is bromine, $R^1$ is hydrogen, $R^2$ is hydrogen, $R^3$ is hydrogen, $R^4$ is hydrogen, $R^5$ is hydrogen, $R^6$ is hydrogen, $R^7$ is methyl, $R^8$ is n—$C_3H_7SO_2$ and X is oxygen.

13. The method of claim 10 wherein R is chlorine, $R^1$ is hydrogen, $R^2$ is hydrogen, $R^3$ is hydrogen, $R^4$ is hydrogen, $R^5$ is hydrogen, $R^6$ is hydrogen, $R^7$ is methyl, $R^8$ is $C_2H_5SO_2$ and X is oxygen.

14. The method of claim 10 wherein R is chlorine, $R^1$ is hydrogen, $R^2$ is hydrogen, $R^3$ is hydrogen, $R^4$ is hydrogen, $R^5$ is hydrogen, $R^6$ is hydrogen, $R^7$ is methyl, $R^8$ is n—$C_3H_7SO_2$ and X is oxygen.

15. The method of claim 10 wherein R is bromine, $R^1$ is methyl, $R^2$ is methyl, $R^3$ and $R^4$ together are carbonyl, $R^5$ is methyl, $R^6$ is methyl, $R^7$ is methyl, $R^8$ is bromine and X is sulfur.

16. The method of claim 10 wherein R is bromine, $R^1$ is hydrogen, $R^2$ is hydrogen, $R^3$ is methyl, $R^4$ is hydrogen, $R^5$ is hydrogen, $R^6$ is hydrogen, $R^7$ is methyl, $R^8$ is $C_2H_5SO_2$ and X is oxygen.

17. An herbicidal composition comprising an herbicidally effective amount of a compound having the structural formula

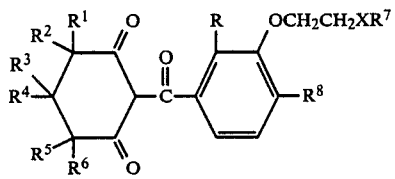

wherein
X is oxygen or sulfur;
R is chlorine or bromine;
$R^1$ is hydrogen or $C_1$-$C_4$ alkyl;
$R^2$ is hydrogen or $C_1$-$C_4$ alkyl;
$R^3$ is hydrogen or $C_1$-$C_4$ alkyl;
$R^4$ is hydroxy, hydrogen or $C_1$-$C_4$ alkyl; or
$R^3$ and $R^4$ together are carbonyl (=O) with the proviso that $R^1$, $R^2$, $R^5$ and $R^6$ are all $C_1$-$C_4$ alkyl;
$R^5$ is hydrogen or $C_1$-$C_4$ alkyl;
$R^6$ is hydrogen, $C_1$-$C_4$ alkyl, $C_1$-$C_4$ alkylthio or $C_1$-$C_4$ alkylsulfonyl;
$R^7$ is methyl or ethyl; and
$R^8$ is (1) halogen; (2) nitro; or (3) $R^bSO_n$— wherein n is the integer 0 or 2 ; and $R^b$ is (a) $C_1$-$C_3$ alkyl; and a salt thereof and an inert carrier therefor.

18. The herbicidal composition of claim 17 wherein R is chlorine or bromine; $R^1$ is hydrogen or methyl; $R^2$ is hydrogen or methyl; $R^3$ is hydrogen or methyl; $R^4$ is hydrogen or methyl or $R^3$ or $R^4$ together are carbonyl with the proviso that $R^1$, $R^2$, $R^5$ and $R^6$ are all methyl; $R^5$ is hydrogen or methyl; $R^6$ is hydrogen, methyl, methylthio or methyl sulfonyl; $R^7$ is methyl or ethyl; $R^8$ is hydrogen; chlorine, bromine, nitro or $R^bSO_2$ wherein $R^b$ is $C_1$-$C_3$ alkyl.

19. The herbicidal composition of claim 18 wherein R is bromine, $R^1$ is methyl, $R^2$ is methyl, $R^3$ is hydrogen, $R^4$ is hydrogen, $R^5$ is hydrogen, $R^6$ is hydrogen, $R^7$ is methyl, $R^8$ is bromine and X is oxygen.

20. The herbicidal composition of claim 18 wherein R is bromine, $R^1$ is hydrogen, $R^2$ is hydrogen, $R^3$ is hydrogen, $R^4$ is hydrogen, $R^5$ is hydrogen, $R^6$ is hydrogen, $R^7$ is methyl, $R^8$ is n—$C_3H_7SO_2$ and X is oxygen.

21. The herbicidal composition of claim 18 wherein R is chlorine, $R^1$ is hydrogen, $R^2$ is hydrogen, $R^3$ is hydrogen, $R^4$ is hydrogen, $R^5$ is hydrogen, $R^6$ is hydrogen, $R^7$ is methyl, $R^8$ is $C_2H_5SO_2$ and X is oxygen.

22. The herbicidal composition of claim 18 wherein R is chlorine, $R^1$ is hydrogen, $R^2$ is hydrogen, $R^3$ is hydrogen, $R^4$ is hydrogen, $R^5$ is hydrogen, $R^6$ is hydrogen, $R^7$ is methyl, $R^8$ is n—$C_3H_7SO_2$ and X is oxygen.

23. The herbicidal composition of claim 18 wherein R is bromine, $R^1$ is methyl, $R^2$ is methyl, $R^3$ and $R^4$ together are carbonyl, $R^5$ is methyl, $R^6$ is methyl, $R^7$ is methyl, $R^8$ is bromine and X is sulfur.

24. The herbicidal composition of claim 18 wherein R is bromine, $R^1$ is hydrogen, $R^2$ is hydrogen, $R^3$ is methyl, $R^4$ is hydrogen, $R^5$ is hydrogen, $R^6$ is hydrogen, $R^7$ is methyl, $R^8$ is $C_2H_5SO_2$ and X is oxygen.

* * * * *

UNITED STATES PATENT AND TRADEMARK OFFICE
CERTIFICATE OF CORRECTION

PATENT NO. : 4,957,538
DATED : September 18, 1990
INVENTOR(S) : William J. Michaely It is certified that error appears in the above-indentified patent and that said Letters Patent is hereby corrected as shown below:

On the title page, item (54): "CYCLOOHEXANEDIONES" should read --CYCLOHEXANEDIONES--.

In Column 32, line 44, "$c_1$" should read --$C_1$--. Insert "is" after "R".

In Column 32, line 46, "$c_4$" should read --$C_4$--.

In Column 32, line 63, insert --R is bromine,-- after the word "wherein".

Signed and Sealed this

Fifth Day of April, 1994

BRUCE LEHMAN

Attest:

Attesting Officer

Commissioner of Patents and Trademarks